(12) United States Patent
Gajate et al.

(10) Patent No.: US 6,583,127 B1
(45) Date of Patent: Jun. 24, 2003

(54) USE OF ETHERLYSOPHOSPHOLIPIDS AS ANTIINFLAMMATORY AGENTS

(75) Inventors: Consuelo Gajate, Salamanca (ES); Jose Camprubi, Barcelona (ES)

(73) Assignee: Inkeysa. SA, Barcelona (ES)

( * ) Notice: Subject to any disclaimer, the term of this patent is extended or adjusted under 35 U.S.C. 154(b) by 0 days.

(21) Appl. No.: 09/868,571

(22) PCT Filed: Dec. 20, 1999

(86) PCT No.: PCT/EP99/10122

§ 371 (c)(1),
(2), (4) Date: Aug. 23, 2001

(87) PCT Pub. No.: WO00/37088

PCT Pub. Date: Jun. 29, 2000

(30) Foreign Application Priority Data

Dec. 21, 1998 (EP) .............................................. 98124340

(51) Int. Cl.⁷ ............................................. A61K 31/685
(52) U.S. Cl. ........................................ 514/77; 514/838
(58) Field of Search ............................................ 514/77

(56) References Cited

U.S. PATENT DOCUMENTS

| 5,266,564 A | | 11/1993 | Modolell et al. .............. 514/77 |
| 5,942,246 A | | 8/1999 | Mayhew et al. ............. 424/450 |
| 5,965,159 A | | 10/1999 | Mayhew et al. ............. 424/450 |
| 6,071,919 A | * | 6/2000 | Theodore et al. ........... 424/531 |
| 6,172,050 B1 | * | 1/2001 | Nossner et al. ................ 514/79 |

FOREIGN PATENT DOCUMENTS

| WO | 87/01257 | 3/1987 |
| WO | 96/11670 | 4/1996 |

* cited by examiner

Primary Examiner—James H. Reamer
(74) Attorney, Agent, or Firm—Foley & Lardner

(57) ABSTRACT

The present invention relates to the use of a series of etherlysophospholipids (ELPs) for the preparation of a medicament for the treatment of an inflammatory disease without causing adverse gastrointestinal side effects and/or without inhibition of phospholipase $A_2$ and prostaglandin $E_2$, as well as preventing or treating ulcerative conditions of the gastrointestinal tract.

23 Claims, 10 Drawing Sheets

USE OF ETHERLYSOPHOSPHOLIPIDS AS ANTIINFLAMMATORY AGENTS

Figure 1:
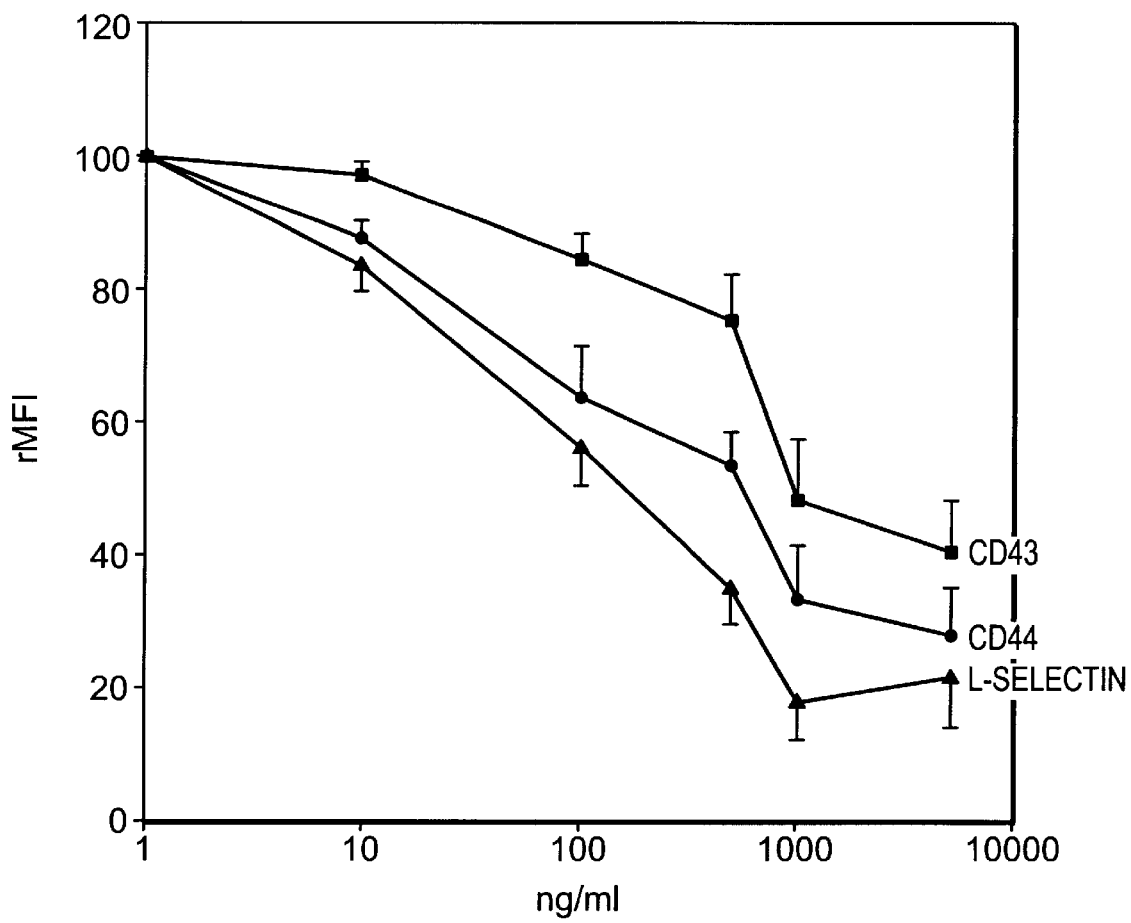

This specification recites a number or prior art documents. The disclosure content of said documents is herewith incorporated by reference.

The present invention relates to the use of etherlysophospholipids (ELPs) for the preparation of a medicament for the prevention or treatment of an inflammatory disease without causing or essentially without causing adverse gastrointestinal side effects and/or without inhibition of phospholipase $A_2$ and prostaglandin $E_2$, as well as for preventing or treating ulcerative conditions of the gastrointestinal tract.

The inflammatory response is an essential mechanism of defense of the organism against the attack of infectious agents, and it is also implicated in the pathogenesis of many acute and chronic diseases, including autoimmune disorders. In spite of being needed to fight pathogens, the effects of an inflammatory burst can be devastating. It is therefore often necessary to restrict the symptomatology of inflammation with the use of anti-inflammatory drugs.

Inflammation is a complex process normally triggered by tissue injury that includes activation of a large array of enzymes, the increase in vascular permeability and extravasation of blood fluids, cell migration and release of chemical mediators, all aimed to both destroy and repair the injured tissue.

Inflammation is commonly treated with so-called non-steroid anti-inflammatory drugs (NSAIDs). Although chemically diverse, all NSAIDs act by inhibiting cyclooxygenase (COX) activity, thus resulting in suppression of the production of inflammatory prostaglandins (PG). Two cyclooxygenase enzymes, named COX-1 and COX-2, have been described, which catalyze the synthesis of prostaglandins from arachidonic acid [Xie et al., Proc. Natl. Acad. Sci., 88, 2692 (1991)]. COX-1 is expressed in most tissues and is responsible for the synthesis of. PGs needed to maintain gut and kidney integrity, whereas COX-2 is induced at sites of tissue damage, where it leads to the synthesis of inflammatory PGs and other inflammatory mediators [Kargman et al., Gastroenterology, 111, 445 (1996)].

While protecting from inflammatory damage, all NSAIDs tested so far have important gastrointestinal toxic side effects, mostly due to the inhibition of the synthesis of cytoprotective prostaglandins (mainly $PGE_2$). Therefore, anti-inflammatory NSAIDs that act selectively on COX-2, and not on COX-1, have been eagerly searched for and developed. However, COX-2 inhibitors turned out to inhibit inflammation only at concentrations that also inhibited COX-1, and hence provoke mucosal toxicity through suppression of gastric $PGE_2$ synthesis [Wallace et al., Gastroenterology, 115, 101 (1998)]. Indeed NSAIDs inhibit ulcer healing by interfering with the synthesis of growth factors involved in repair of the gastric mucosa. For example, it has been shown that indomethacin, a potent NSAID, inhibits the production of PGs and of Hepatocyte Growth Factor (HGF), a mediator of epithelial growth and angiogenesis at the site of ulcerative mucosal erosion [Bamba et al., Biochem. Biophys. Res. Comm., 245, 567 (1998)].

Furthermore, the finding that gene-targeted, COX-2 deficient mice are still able to mount a normal inflammatory response, but suffer from kidney dysfunction [Morham et at., Cell, 83, 473 (1995)] has additionally challenged the selective inhibition of COX-2.

Finally, as a result of the inhibition of PG synthesis, the accumulative increase in arachidonic acid enhances the production of leukotrienes by the lipooxygenase enzyme, thus resulting in vasoconstriction, a life-threatening side effect in individuals with asthmatic or circulatory complications [Fosslien E., Annals Clin. & Lab. Science, 28, 67 (1998)].

A further group of NSAIDs named etherlysophospholipids (ELPs) or alkyl-lysophospholipids (ALPs) are known for their antineoplastic properties (DE 2,619,686), in particular ET-18-OCH$_3$ (also known as edelfosine) having the formula:

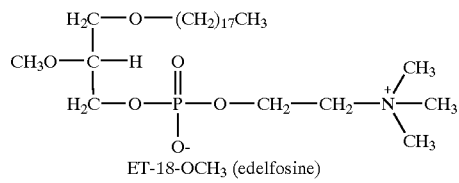

ET-18-OCH$_3$ (edelfosine)

Edelfosine, one of the best studied ELPs, has been shown to induce cell death by apoptosis selectively on tumor cells, while sparing normal, non-transformed cells [Mollinedo et al., Cancer Res., 57, 1320 (1997)]. Edelfosine and several other ether lipid compounds have undergone phase I/II clinical evaluation for the treatment of cancer or their use as purging agents in autologous bone marrow transplantation [Lohmeyer et al., Drugs of the Future, 19, 1021 (1994)].

Moreover, U.S. Pat. No. 5,266,564 discloses the use of a series of ELPs, including several compounds used in accordance with the present invention, in the treatment of autoimmune diseases, such as rheumatoid arthritis and ankylosing spondylitis.

EP 236,390 B discloses the use of such compounds in the treatment of multiple sclerosis, another autoimmune illness.

From DE 3,941,009 the effectiveness of edelfosine to eliminate activated lymphocytes is known.

Recently, Bosse et al. [Pathobiology, 63, 109 (1995)] have described the selective inhibition of adhesion molecule expression in vitro by edelfosine on endothelial cells. Potential anti-inflammatory properties of edelfosine have been mentioned from such capacity of inhibition, but according to the cited article, the in vivo anti-inflammatory activity of edelfosine was not tested in animal models. As is well known in the art, the pharmaceutical in vivo activity of a compound including the potential occurrence of adverse side effects cannot be predicted from in vitro data without further ado.

Thus, no NSAID is available to date that combines potent in vivo anti-inflammatory properties with the lack or a minimum of toxic side effects on the gastrointestinal mucosa [Cryer et al., Am. J. Med., 104, 413 (1998)]. Accordingly, there is a need in the art to develop effective anti-inflammatory agents that are free of or essentially free of toxic gastrointestinal side effects for in vivo therapy in mammals, preferably humans.

The solution to this technical problem is achieved by providing the embodiments characterized in the claims.

Accordingly, the present invention relates to the use of a compound of formula (I):

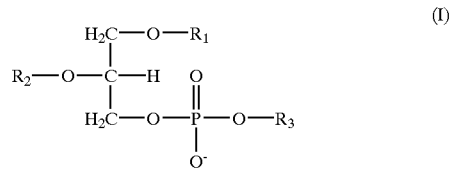

wherein $R_1$ is a $C_{12}$–$C_{18}$ straight or branched alkyl group;
$R_2$ is $C_1$–$C_8$ straight or branched alkyl group;
and $R_3$ is:

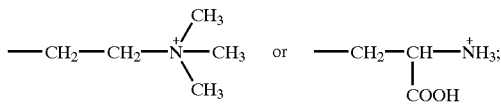

or the salts, enantiomers and diastereomers thereof, for the preparation of a pharmaceutical composition for the prevention or treatment of an inflammatory disease.

Unexpectedly, it has now been found that the above recited compounds are useful in the treatment of an inflammatory disease in mammals and do not inhibit the synthesis of prostaglandins, in particular prostaglandin $E_2$. It was surprisingly and additionally found that synthesis of phospholipase A is not inhibited. Most advantageously, they do not cause or they essentially do not cause adverse gastrointestinal side effects, thereby obviating the disadvantages associated with the use of traditional NSAIDs. Furthermore, surprisingly it has now been found that the recited compounds are useful in the prevention or treatment of ulcerative conditions of the gastrointestinal tract in mammals. The mammals to which these pharmaceutical compositions are preferably administered are humans. The term "essentially not causing adverse side effects" means, in accordance with the present invention, that the overall well-being of the subject treated is not impaired as a consequence of the administration of the pharmaceutical composition of the invention.

The compounds of formula (I) have one or more asymmetric centres and thus they can exist as enantiomers or diastereomers. The pharmaceutical composition prepared in accordance with the present invention may include both mixtures of and separate individual isomers.

The compounds of formula (I) can be obtained in the form of salts of formulas (Ia) or (Ib)

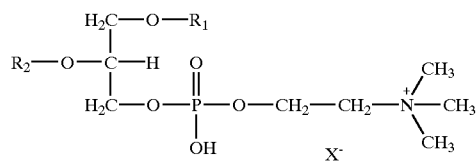

(Ia)

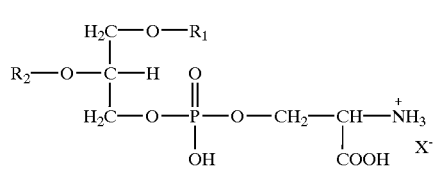

(Ib)

wherein $X^-$ is a pharmaceutically acceptable anion, such as chloride, bromide or iodide, and $R_1$ and $R_2$ have the above mentioned meanings, or of formulas (Ic) or (Id)

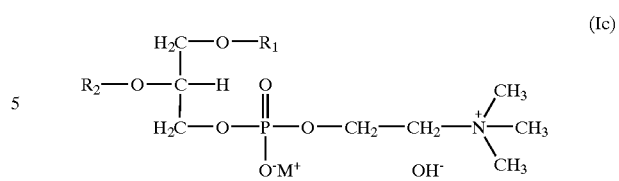

(Ic)

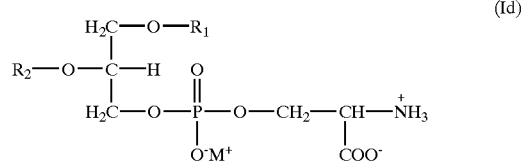

(Id)

wherein $M^+$ is an alkali metal cation (e.g. $Na^+$, $K^+$) or represents a half amount of an alkaline-earth metal cation (e.g. ½ $Ca^{2+}$, ½ $Mg^{2+}$), and $R_1$ and $R_2$ have the above mentioned meanings.

In a preferred embodiment of the use of the invention the compounds of formula (I) are those wherein $R_1$ is $C_{16}$–$C_{18}$ straight alkyl group and $R_2$ is methyl.

In a particularly preferred embodiment of the use of the invention the compound is the compound of formula:

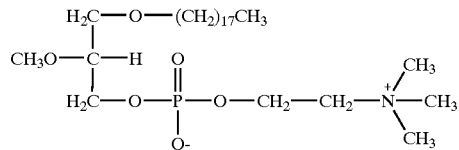

In another particularly preferred embodiment of the use of the invention, the compound is the compound of formula:

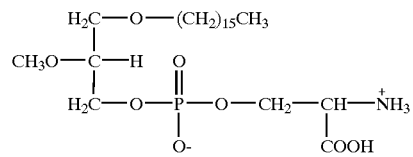

In another preferred embodiment of the use of the invention said inflammatory disease is a chronic inflammatory disease.

In a further preferred embodiment of the use of the present invention, said inflammatory disease is associated with an ulcerative condition of the gastrointestinal tract.

In a particularly preferred embodiment of the use of the invention said chronic inflammatory disease is associated with inflammatory bowel diseases, particularly ulcerative colitis or Crohn's disease.

In another particularly preferred embodiment of the use of the invention said chronic inflammatory disease is associated with inflammatory diseases of the respiratory ways, like asbestosis or silicosis, inflammatory processes derived from alcoholic liver, like liver cirrhosis, and other inflammatory diseases, like pemphigus vulgaris, polymyositis-dermatomyositis, Sjogren-syndrome, Lyme disease, lupus erythematosus or Behget's disease.

In another further preferred embodiment of the use of the invention said inflammatory disease is an acute inflammatory disease, particularly associated with infective diseases, non-rheumatic inflammation, like bursitis, synovitis, capsulitis, tendinitis and/or other inflammatory lesions of traumatic and/or sportive origin.

The present invention further relates to a method of preparing a medicament effective in the prevention or treatment of an inflammatory disease without causing or essentially without causing adverse gastrointestinal side effects comprising the step of formulating a compound of formula (I) into a pharmaceutically acceptable carrier.

The preparation of the compounds of formula (I) according to the present invention can be performed in one of the ways which have been described in the literature, for example, Berchtold R., *Chem. Phys. Lipids*, 30, 389 (1982); Woolley P. and Eibl H., *Chem. Phys. Lipids*, 47, 55 (1988); and Eibl H., *Chem. Phys. Lipids*, 26, 405 (1980).

The invention furthermore relates to a method for the prevention or treatment of an inflammatory trait comprising administering an effective amount of formula (I):

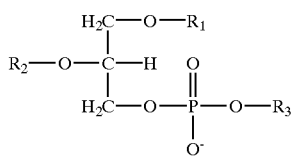

Wherein $R_1$ is a $C_{12}$–$C_{18}$ straight or branched alkyl group;
$R_2$ is $C_1$–$C_8$ straight or branched alkyl group;
and $R_3$ is:

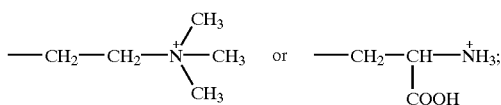

or the salts, enantiomers and diastereomers thereof, to a patient in need thereof.

In a preferred embodiment of the method of the present invention $R_1$ is a $C_{16}$–$C_{18}$ straight alkyl group and $R_2$ is methyl.

In a particularly preferred embodiment of the method of the present invention the compound of formula (I) is:

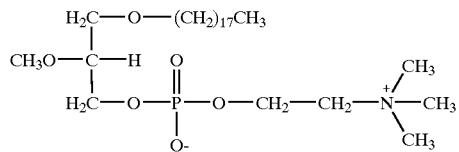

In another particularly preferred embodiment of the method of the present invention the compound of formula (I) is:

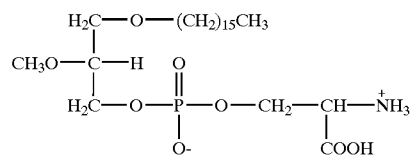

In another preferred embodiment of the method of the present invention said inflammatory disease is a chronic inflammatory disease.

In a further preferred embodiment of the method of the present invention said inflammatory disease is associated with an ulcerative condition of the gastrointestinal tract.

In a particularly preferred embodiment of the method of the present invention said chronic inflammatory disease or said ulcerative condition is associated with an inflammatory bowel disease.

In a further particularly preferred embodiment of the method of the present invention said inflammatory bowel disease is ulcerative colitis, Crohn's disease, a gastric ulcer or a duodenal ulcer.

In another particularly preferred embodiment of the method of the present invention said chronic inflammatory disease is associated with inflammatory diseases of the respiratory ways like asbestosis or silicosis.

In an additional particularly preferred embodiment of the method of the present invention said chronic inflammatory disease is associated with inflammatory processes derived from alcoholic liver, like liver cirrhosis.

In a further particularly preferred embodiment of the method of the present invention said chronic inflammatory disease is associated with other inflammatory diseases, like pemphigus vulgaris, polymyositis-dermatomyositis, Sjögren-syndrome, Lyme disease, lupus erythematosus or Behçet's disease.

The invention in another preferred embodiment relates to a method wherein said inflammatory disease is an acute inflammatory disease.

In a particularly preferred embodiment of the method of the present invention said acute inflammatory disease is associated with infective diseases, non-rheumatic inflammation, like bursitis, synovitis, capsulitis, tendinitis and/or other inflammatory lesions of traumatic and/or sportive origin.

For the intended therapeutic uses, the compounds of the invention are formulated in suitable pharmaceutical compositions, which may further comprise a pharmaceutically acceptable carrier and/or diluent. Examples of suitable pharmaceutical carriers are well known in the art and include phosphate buffered saline solutions, water, emulsions, such a oil/water emulsions, various types of wetting agents, sterile solutions etc. Compositions comprising such carriers can be formulated by well-known conventional methods. These pharmaceutical compositions can be administered to the subject at a suitable dose. Administration of the suitable compositions may be effected by different ways, e.g., by oral, intravenous, intraperitoneal, subcutaneous, intramuscular, topical, intradermal, intranasal or intrabronchial administration. The attending physician and clinical factors will determine the dosage regimen. As it is well known, pharmaceutical dosages for any one patient depend upon many factors, including the patient size, body surface area, age, the particular compound to be administered, sex, time and route of administration, general health, and others drugs being administered concurrently. A typical dose can be, for example, in the range of 1 to 100 mg, preferably 10 to 50 mg; however, doses below or above these ranges are envisioned, especially considering the aforementioned factors. Generally, the regimen as a regular administration of the pharmaceutical composition should be in the range of 1 to 100 mg units, preferably 10 to 50 mg units per day. If the regimen is a continuous infusion, it should also be in the range of 1 μg to 10 mg units per kilogram of body weight per minute, respectively. Progress can be monitored by periodic assessment. The compositions of the invention may be administrated locally or systemically. Administration will be generally oral or parenteral. Preparations for oral or parenteral administration include pharmaceutical solid forms, aqueous or non-aqueous solutions, suspensions, and emulsions. Examples of solids forms include pellets, tablets, pills, powders, capsules, and any other galenic solid form. Examples of non-aqueous solvents are propylene glycol, polyethylene glycol, vegetable oils such a olive oil, and injectable organic esters such a ethyl oleate. Aqueous carriers include water, alcoholic/aqueous solutions, emulsions or suspensions, including saline and buffered media. Parenteral vehicles include sodium chloride solution, Ringer's dextrose and sodium chloride, lactated Ringer's, or fixed oils. Intravenous vehicles fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

In accordance with the present invention it was found that the use of the compounds of the invention presents the following advantages: (i) the anti-inflammatory potential of the compounds of the invention in vivo in an animal model is superior to that of currently used potent NSAIDs; (ii) "in vitro" experiments indicate that the compounds of the invention down-regulate the cell surface expression of adhesion molecules (CD43, CD44 and L-selectin-CD62L-) in human peripheral blood neutrophils; (iii) the anti-inflammatory properties of the compounds of the invention are not related to their tumoricidal properties, as non-cytotoxic ELPs retain full anti-inflammatory capacity; (iv) surprisingly and unexpectedly, the compounds of the invention exert their anti-inflammatory function without affecting the production of $PGE_2$ and the activity and expression of COX-1 and COX-2, and hence are free of the gastrointestinal ulceration side effects of the known NSAIDs. Furthermore, the compounds of the invention do not affect expression of cytosolic $PLA_2$ and are able to increase $PLA_2$ activity; and (V) surprisingly the compounds used in accordance with the invention prevent or treat ulcerative conditions of the gastrointestinal tract.

Furthermore, in accordance with the present invention, it was demonstrated that: (i) the potent anti-inflammatory potential of the compounds used in accordance with the invention in an animal model is superior to the action of indomethacin, one of the most potent NSAID; (ii) at the cellular level, the anti-inflammatory potential was shown to relate to the capacity of the compounds used in accordance with the invention to decrease the expression of adhesion cell surface molecules and to inhibit the formation of free radicals in leukocytes. The L-selectin down-regulation effect of said compounds was higher than that induced by the phorbol ester PMA; (iii) surprisingly, it was also found that the unexpectedly high anti-inflammatory properties of said compounds are not related to the inhibition of the synthesis of the inflammatory prostaglandin $PGE_2$, whereas indomethacin, used as a control, abolishes completely the $PGE_2$ production. Furthermore, the compounds of the invention stimulated $PLA_2$ activity, as measured by [$^3$H] arachidonic acid release. Hence, said compounds fulfill both the requirements of having strong anti-inflammatory potential without affecting the production of gastric mucosa protective prostaglandin; (iv) surprisingly, it was found that said compounds present a good therapeutic potential in an animal model of ulcerative colitis.

It is important to note that the anti-inflammatory treatment with the compounds used in this invention is free of gastrointestinal ulceration side effects. This is due to the lack of inhibition of enzymatic activity of the COX-1 and COX-2 enzymes by the compounds used in this invention which prevents depletion of gastroprotective $PGE_2$ during the anti-inflammatory treatment. Thus, the compound is perfectly applicable for administration in mammals, preferably humans. It is also important to note that the compounds used in the present invention can be used to treat ulcerative conditions of the gastrointestinal tract.

In the examples and figures described below, IEC01 means ET-18-OCH$_3$ or Edelfosine, wherein $R_1$ is a $C_{18}$ straight alkyl group, $R_2$ is a methyl group and $R_3$ is —(CH$_2$)$_2$—N$^+$(CH$_3$)$_3$ and IES01 is a compound of formula (I) wherein $R_1$ is a $C_{16}$ straight alkyl group, $R_2$ is a methyl group and $R_3$ is —CH$_2$—CH(COOH)—N$^+$H$_3$.

The figures show:

FIG. 1: Dose-response of the effect of IEC01 on the cell surface expression of L-selectin, CD43 and CD44 in human neutrophils FIG. 2: Superoxide anion generation in murine macrophages upon treatment with the compounds of the invention.

Figure 3:
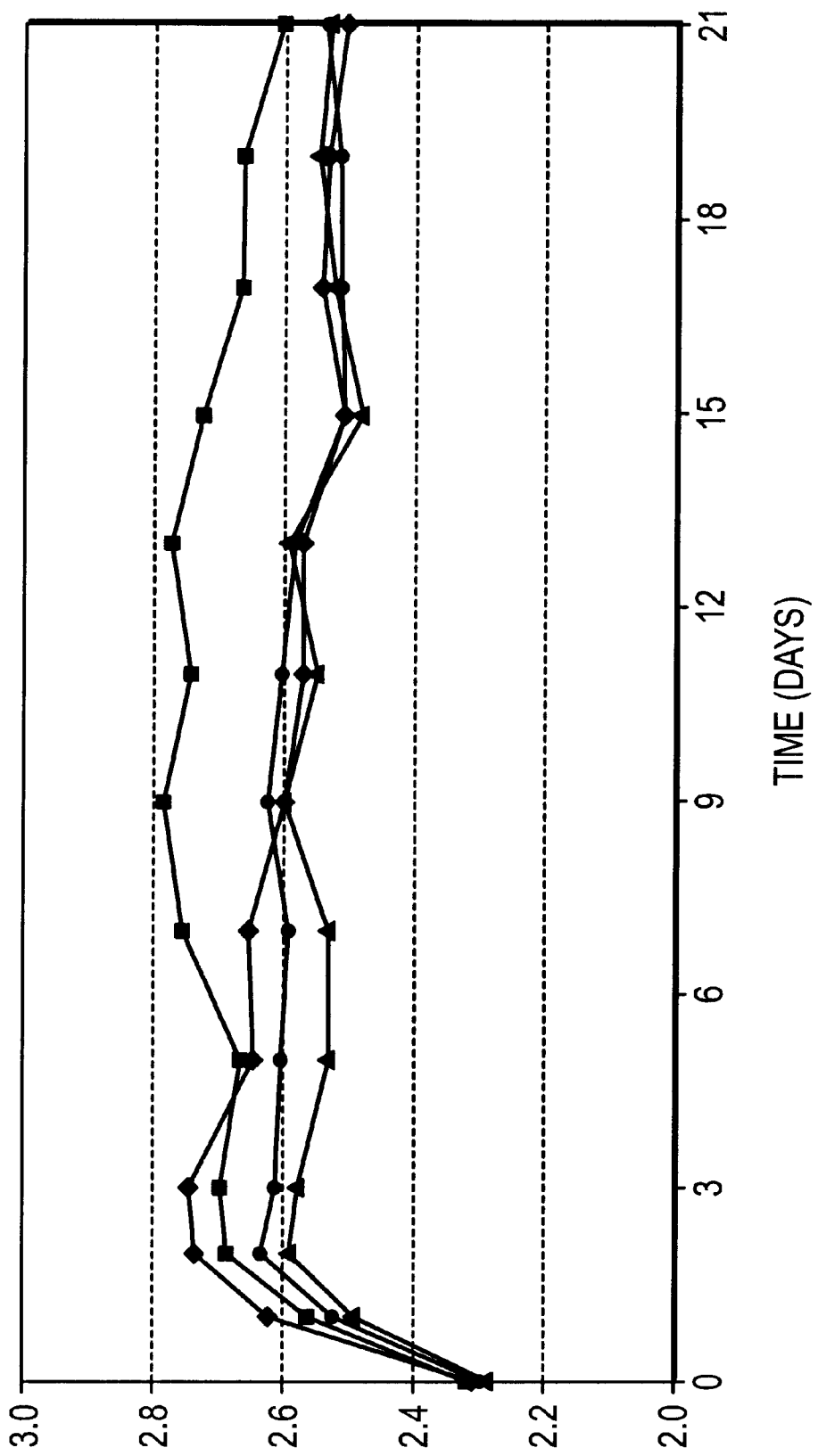

FIG. 3: Anti-inflammatory activity in Bentonite-induced skin edema. Right food pad diameter (mm). Mean values of inflamed control mice (black rectangles); mice treated with indomethacin (diamonds); mice treated with 2.5 mg/Kg (triangles) or 5 mg/kg IES01 (black circles).

Figure 4:
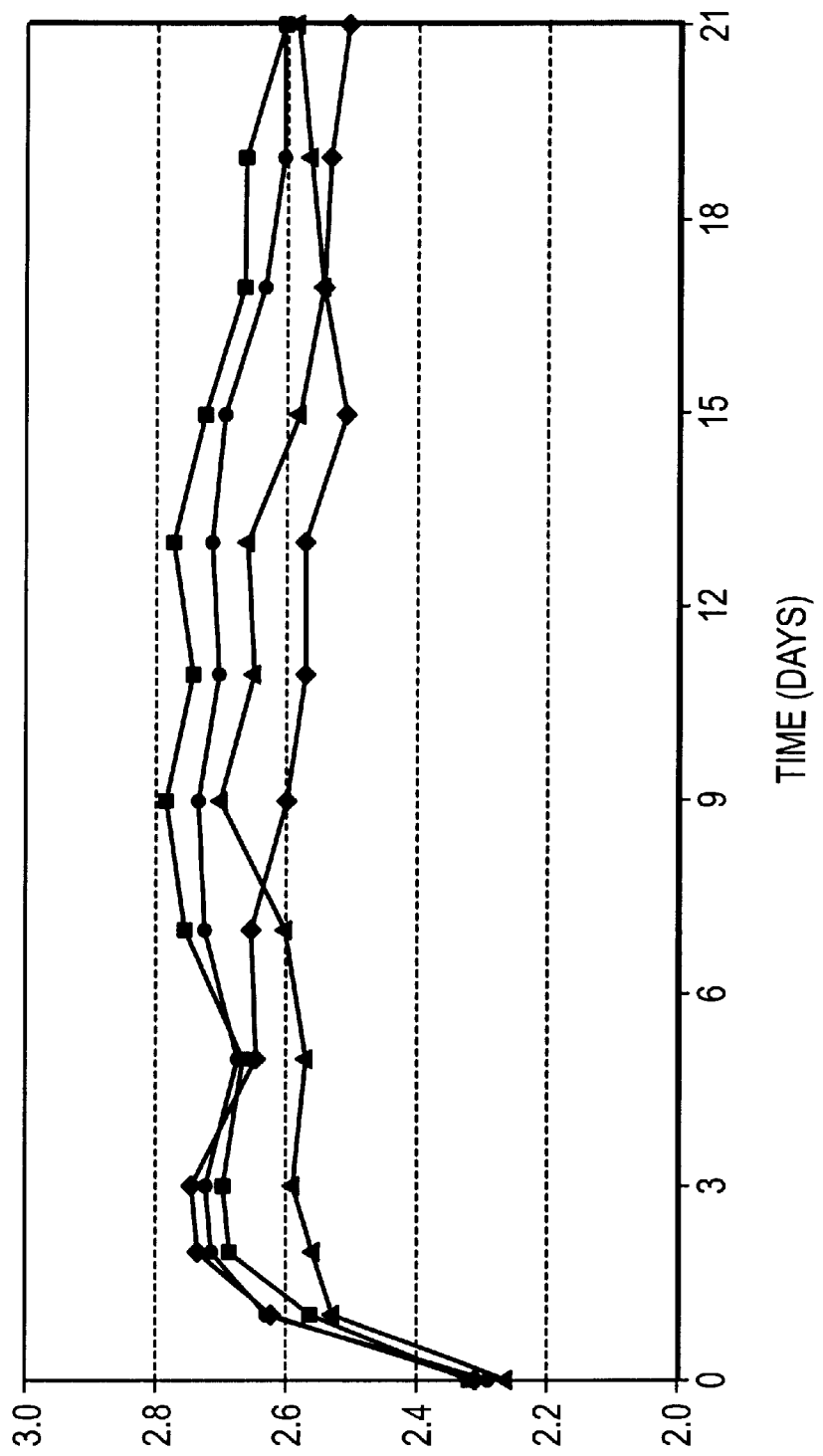

FIG. 4: Anti-inflammatory activity in Bentonite-induced skin edema. Right food pad diameter (mm). Mean values of inflamed control mice (black rectangles); mice treated with indomethacin (diamonds); mice treated with 2.5 mg/kg (triangles) or 5 mg/kg IEC01 (black circles).

Figure 5:
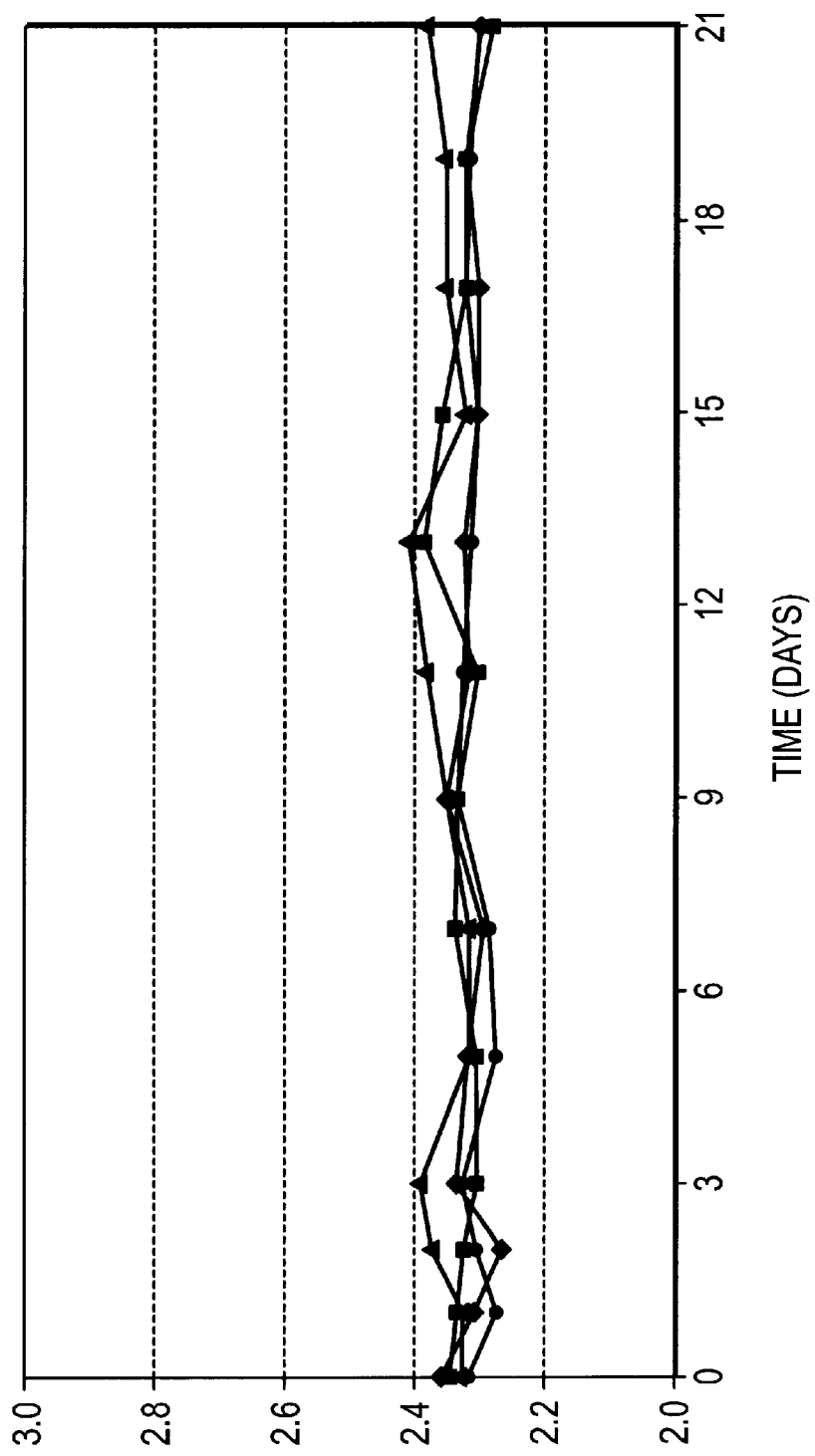

FIG. 5: Anti-inflammatory activity in Bentonite-included skin edema. Left food pad diameter (mm). Mean values of inflamed control mice (black rectangles); mice treated with indomethacin (diamonds); mice treated with 2.5 mg/kg (triangles) or 5 mg/kg IES01 (black circles).

Figure 6:
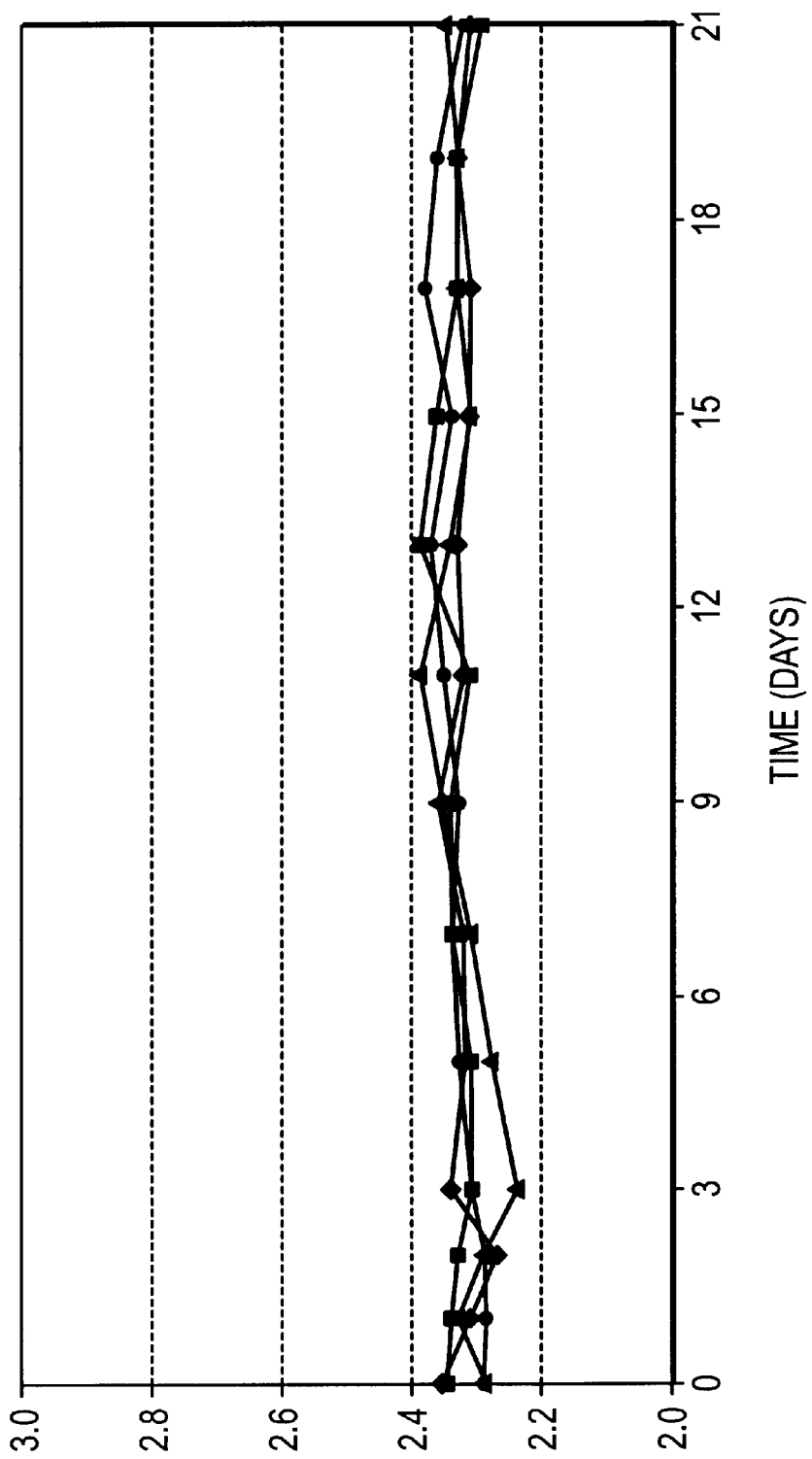

FIG. 6: Anti-inflammatory activity in Bentonite-induced skin edema. Left food diameter (mm). Mean values of inflamed control mice (black rectangles); mice treated with indomethacin (diamonds); mice treated with 2.5 mg/kg (triangles) or 5 mg/kg IE01 (black circles).

Figure 7:
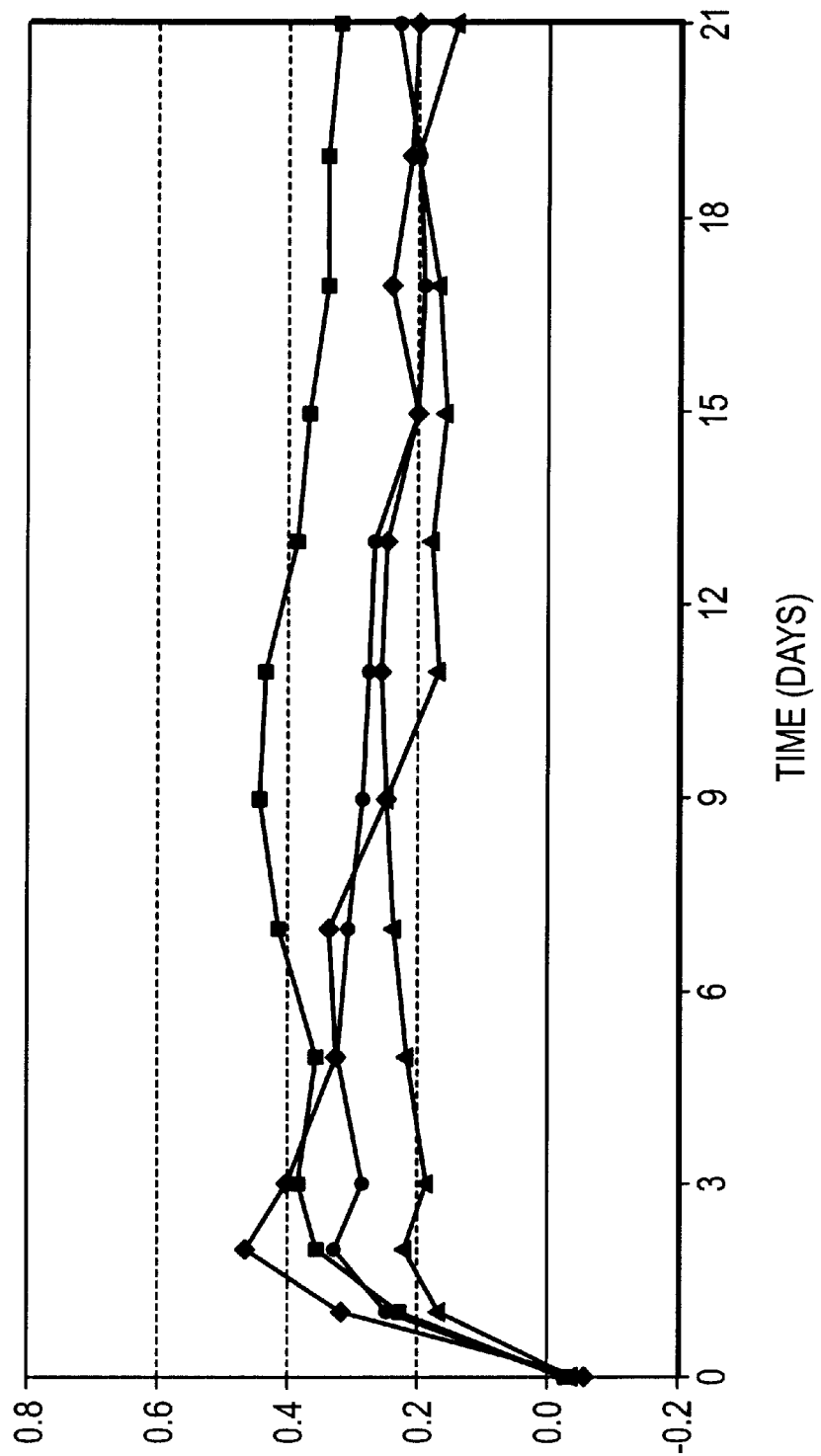

FIG. 7: Anti-inflammatory activity in Bentonite-included skin edema.

Difference between right and left food pad diameter (mm). Mean values of inflamed control mice (black rectangles); mice treated with indomethacin (diamonds); mice treated with 2.5 mg/kg (triangles) or 5 mg/kg IES01 (black circles).

Figure 8:
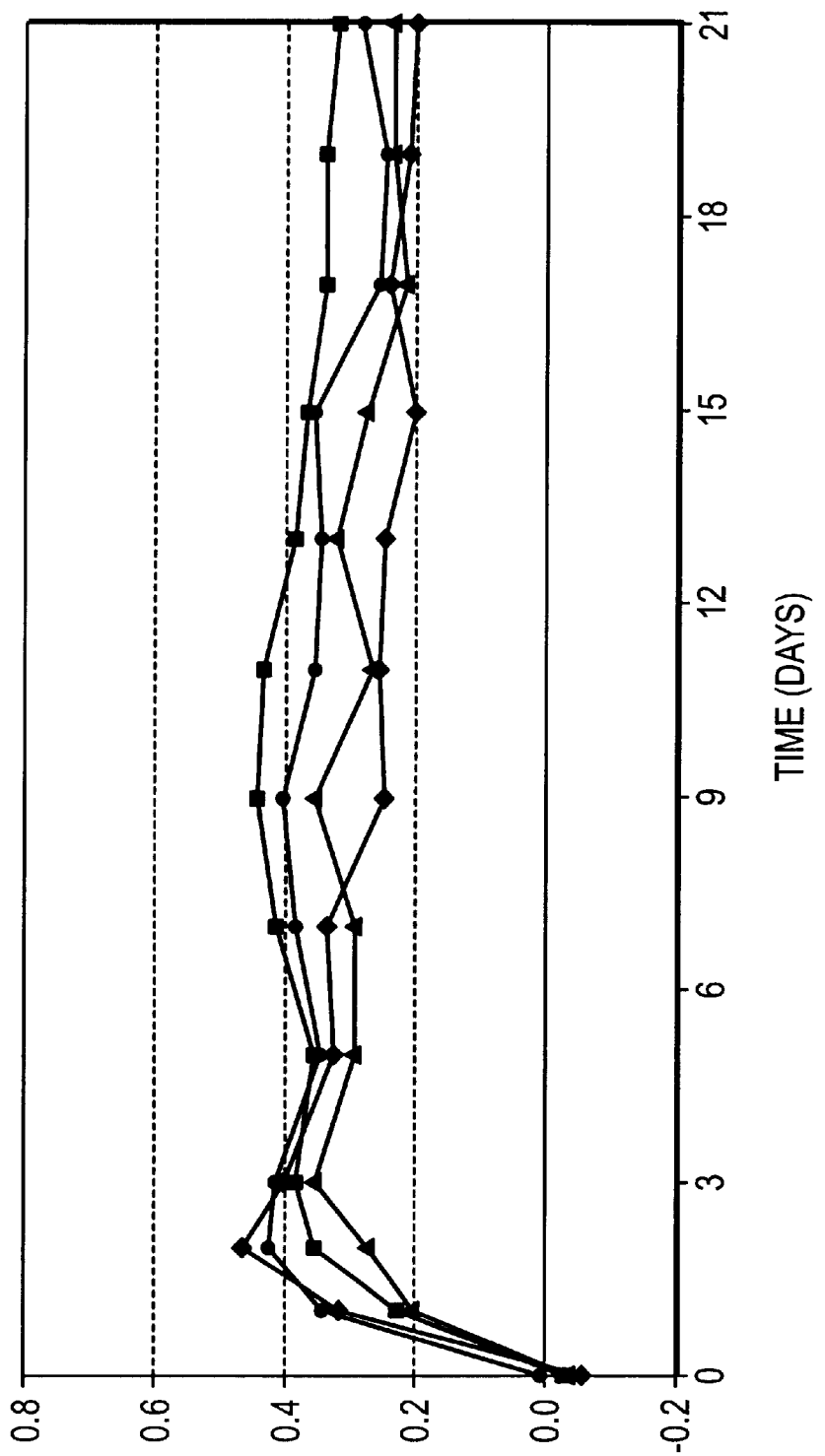

FIG. 8: Anti-inflammatory activity in Bentonite-induced skin edema. Difference between right and left food pad diameter (mm). Mean values of inflamed control mice (black rectangles); mice treated with indomethacin (diamonds); mice treated with 2.5 mg/kg (triangles) or 5 mg/kg IEC01 (black circles).

Figure 9:
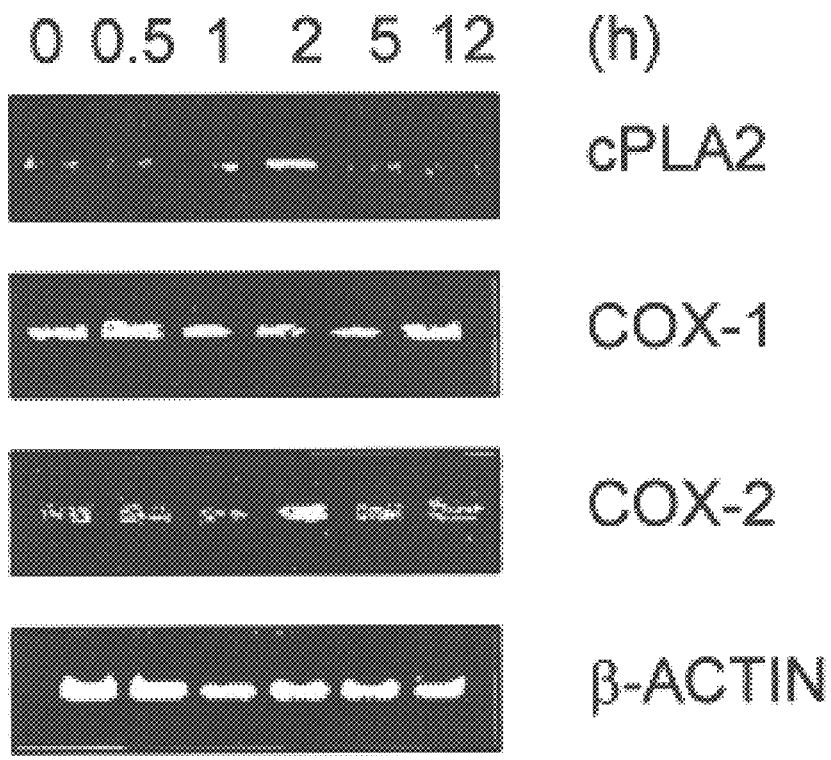

FIG. 9: Expression of cPLA$_2$, COX-1 and COX-2 in HL-60 cells treated with IEC01. PCR amplification of β-actin was used as an internal control. After amplification, the PCR products were electrophoresed onto a 2% agarose gel and stained with ethidium bromide. Experiments shown are representative of three performed.

Figure 10:
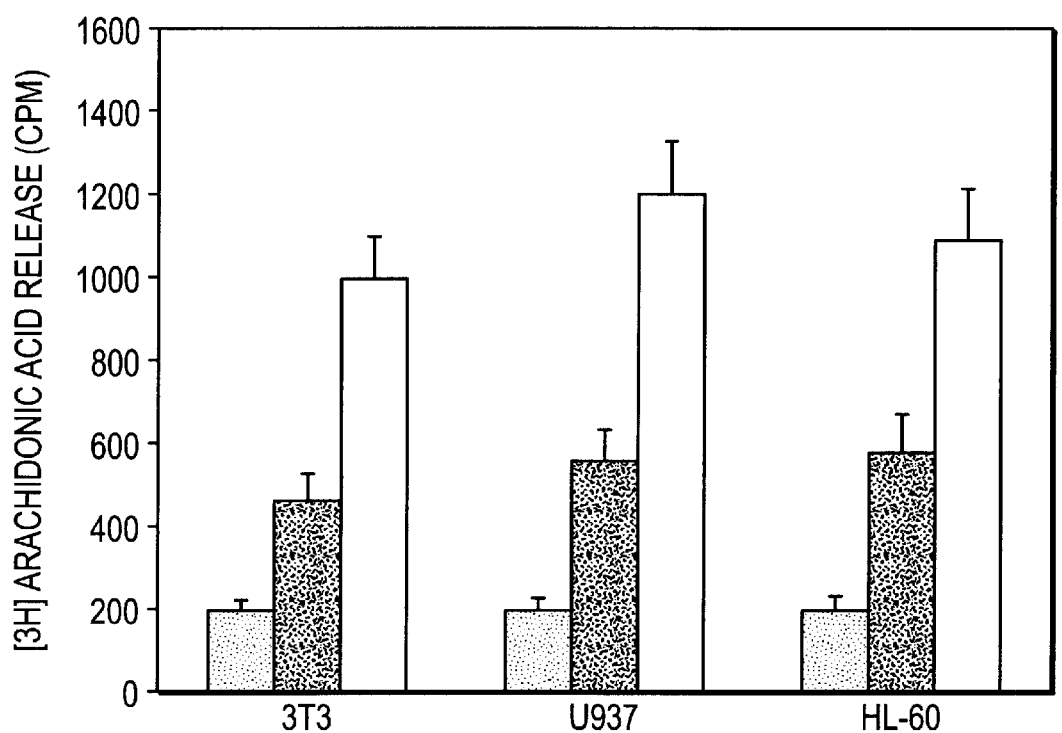

FIG. 10: The release of arachidonic acid is used to assess the enzymatic activity of PLA$_2$. Cells were incubated with [3H] arachidonic acid and treated with ionomycin and IEC01. The radioactivity in the supernatant was measured.

EXAMPLES

The following examples are merely illustrative and are not to be construed as a limitation of the scope of the present invention.

Example 1

Anti-inflammatory Potential

1. Down-regulation of Cell Surface Adhesion Molecules in Human Neutrophils.

Neutrophil-endothelium interaction and the subsequent neutrophil extravasation are essential for the inflammatory response. This process can be divided into three steps: initial interaction of neutrophils with activated endothelium ("rolling"), neutrophil activation with firm adhesion to endothelial cells and, finally, their extravasation into the surrounding tissues. Several adhesion molecules are involved in the process of adhesion and migration of leukocytes through vascular endothelium at sites of inflammation. Among them, L-selectin (CD62L) has a key role in the initial attachment of circulating leukocytes to endothelium.

Method:

Isolation and treatment of neutrophils. Human neutrophils were obtained from fresh peripheral blood by dextran sedimentation and centrifugation on Ficoll-Hypaque followed by hypotonic lysis of residual erythrocytes. The final cell preparation contained more than 98% neutrophils, as assessed by Giemsa-Wright staining. Cells were resuspended at $3\times10^6$ neutrophils/ml in HEPES/glucose buffer (150 mM NaCl, 5 mM KCl, 10 mM HEPES, 1.2 mM $MgCl_2$, 1.3 mM $CaCl_2$, 5.5 mM glucose, pH 7.5), and incubated in the absence or presence of distinct agents at 37° C. for the times indicated in the respective legends to figures. Subsequently, cells were pelleted by centrifugation and saved to determine the content of different cell surface antigens by flow cytometry.

Monoclonal antibodies. The following monoclonal antibodies were used: TS1/11 anti-CD11a, Bear-1 anti-CD11b, TP1/36.1 anti-CD43, HP2/9 anti-CD44, Leu-8 anti-L-selectin, and W6/32, specific for a monomorphic determinant on HLA-A, B molecules. P3X63 myeloma culture supernatant was used as a negative control. The antibodies are commercially available.

Immunofluorescence flow cytometry. Immunofluorescence flow cytometry analysis was performed in a FACStar-Plus and a FACScan flow cytometers (Becton-Dickinson). Neutrophils were incubated at 4° C. with the corresponding monoclonal antibody followed by washing and labelling with a fluorescein isothiocyanate (FITC)-labelled-goat anti-mouse IgG antibody (DAKO, Glostrup, Denmark). Mean fluorescence intensity (MFI) in linear scale was obtained from at least 7000 cells in each sample, and the fluorescence produced by the myeloma P3X63 supernatant was considered as background. Results were expressed as relative MFI (rMFI), such that $$rMFI=(MFI_{agent}\times100)/MFI_{medium}$$

Background fluorescence was substracted from all values.

Results:

We have found that IEC01 is able to induce a strong reduction in the expression of L-selectin (CD62L) on the surface of human neutrophils, as assessed by flow cytometry analysis (FIG. 1). This IEC01-induced L-selectin down-regulation was time- and dose-dependent. The IEC01-induced reduction in the level L-selectin at the neutrophil surface was very potent, even at a concentration of 0.1 µg/ml of IEC01, and reaches a maximum at 1 µg/ml. At this latter concentration, the L-selectin down-regulation effect of IEC01 was higher than that induced by the phorbol ester PMA (see Table 1). The decrease in the cell surface L-selectin content was very rapid and reached a maximum within 5 minutes (data not shown).

TABLE 1

| Treatment | CD11b | CD43 | CD44 | L-Selectin | HLA | CD11a |
|---|---|---|---|---|---|---|
| Medium | 100 | 100 | 100 | 100 | 100 | 100 |
| PMA | | | | | | |
| (10 ng/ml) | 272 ± 22 | 33.5 ± 9 | 49.5 ± 11 | 38 ± 7 | 96 ± 7 | 95 ± 8 |
| IEC01 | | | | | | |
| (10 ng/ml) | 97.5 ± 8.5 | 87.5 ± 2.5 | 97 ± 2 | 83.5 ± 4 | 101 ± 5 | 99 ± 3 |
| (100 ng/ml) | 101 ± 3 | 63 ± 8 | 84 ± 4 | 56 ± 6 | 100 ± 4 | 102 ± 5 |
| (500 ng/ml) | 103 ± 3 | 53 ± 5 | 75 ± 7 | 35 ± 5.5 | 99 ± 5 | 97 ± 8 |
| (1 µg/ml) | 105 ± 6 | 33 ± 8 | 48 ± 9 | 18 ± 6 | 102 ± 6 | 101 ± 6 |
| (5 µg/ml) | 130 ± 15 | 28 ± 7 | 40 ± 8 | 22 ± 8 | 101 ± 5 | 96 ± 5 |

The cell surface expression of other adhesion molecules, such as CD43 and CD44, was also decreased, though to a lesser extent than L-selectin, by treatment of human neutrophils with IEC01 (FIG. 1). Treatment of neutrophils with IEC01 did not alter the expression of other cell surface antigens, including CD11a and HLA (Table 1). The neutrophil surface expression of CD11b was unaffected upon IEC01 treatment within the range of concentrations exerting a strong reduction of L-selectin (Table 1), but was slightly upregulated following treatment with 5 µg/ml IEC01, an effect possibly related to a certain degree of neutrophil activation (Table 1). Concentrations of IEC01 higher than 50 µg/ml are toxic for neutrophils.

Conclusions:

The inhibitory effect on the expression of adhesion molecules has been previously described for different NSAIDs [Diaz-González et al., *J. Clin. Invest.*, 95, 1756 (1995); García-Vicuña et al., *Arthr. Rheum.*, 40, 143 (1997); González-Alvaro et al., *J. Rheumatol.*, 23, 723 (1996)], aceclofenac being the most potent drug [González-Alvaro et al., *J. Rheumatol.*, 23, 723 (1996)]. However we show here IEC01 has a significantly higher inhibitory potential than aceclofenac. The $IC_{50}$ of IEC01 for L-selectin down-regulation is about 0.1 µg/ml (FIG. 1), whereas the corresponding $IC_{50}$ of aceclofenac for the same cell surface antigen is 5 µg/ml [González-Alvaro et al., *J. Rheumatol.*, 23, 723 (1996)]. After correcting for the different molecular weights of both compounds, IEC01 results to be 100 times more effective that aceclofenac in promoting L-selectin down-regulation, as the $IC_{50}$ of aceclofenac and IEC01 are $1.41\times10^{-2}$ and $1.94\times10^{-4}$ mM, respectively.

Therefore, we demonstrate that the ELP IEC01 interferes very efficiently with the expression of L-selectin on human neutrophils, promoting a rapid and potent down-regulation of this adhesion molecule from the neutrophil surface. Thus, IEC01 is able to reduce the cell surface expression of an adhesion molecule known to be critical in the early stages of the inflammatory response. Thus, as L-selectin level is drastically reduced at the cell surface of neutrophils, these cells would fail to interact with the endothelium through the "rolling" process, blocking neutrophil extravasation, and thereby the inflammatory response. Furthermore, IEC01 causes also a reduction, though to a lower extent, of other adhesion molecules, like CD43 and CD44 (see Table 1 and FIG. 1). We exclude that the effects observed by the treatment with IEC01 result from unspecific neutrophil activation, since cell surface expression of CD11b was not affected at doses of IEC01 that were inhibitory for L-selectin, CD43 and CD44 (Table 1). In addition, the fact that other cell surface antigens, such as CD11a and HLA, were not affected supports the notion that IEC01 exert a specific action on adhesion receptor expression in neutrophils, which might account, at least in part, for the anti-inflammatory activities of ELPs.

2. Inhibition of Free Radicals Formation

The formation of free superoxide radicals represents an important factor of the inflammatory process both at the tissue and vascular level. Therefore we determined whether the compounds of the invention of the formula are also effective inhibitors of superoxide anions in macrophages.

Method:

Mouse bone marrow derived macrophages were incubated for 24 h at $37°$ C. in MEM+10% FCS to a concentration of $10^6$ cells/ml in the absence or presence of ELPs IES01 and IEC01 at the concentration of 1 or 3 μg/ml. The $O_2^-$ free radicals were measured in a chemoluminescent assay that detects the photons generated by the reaction of superoxid anions with lucigenin. The liberated photons are counted with a luminometer Microlumat LB96P, Berthold, Wildbad, Germany. Collected macrophages are resuspended in 0.2 ml at a concentration of $10^6$/ml in HEPES buffered medium containing 540 μg/ml lucigenin. Superoxid production is initiated by adding 50 mg of Zymosan and the emission of photons is measured with a luminometer for 2 h.

Figure 2:
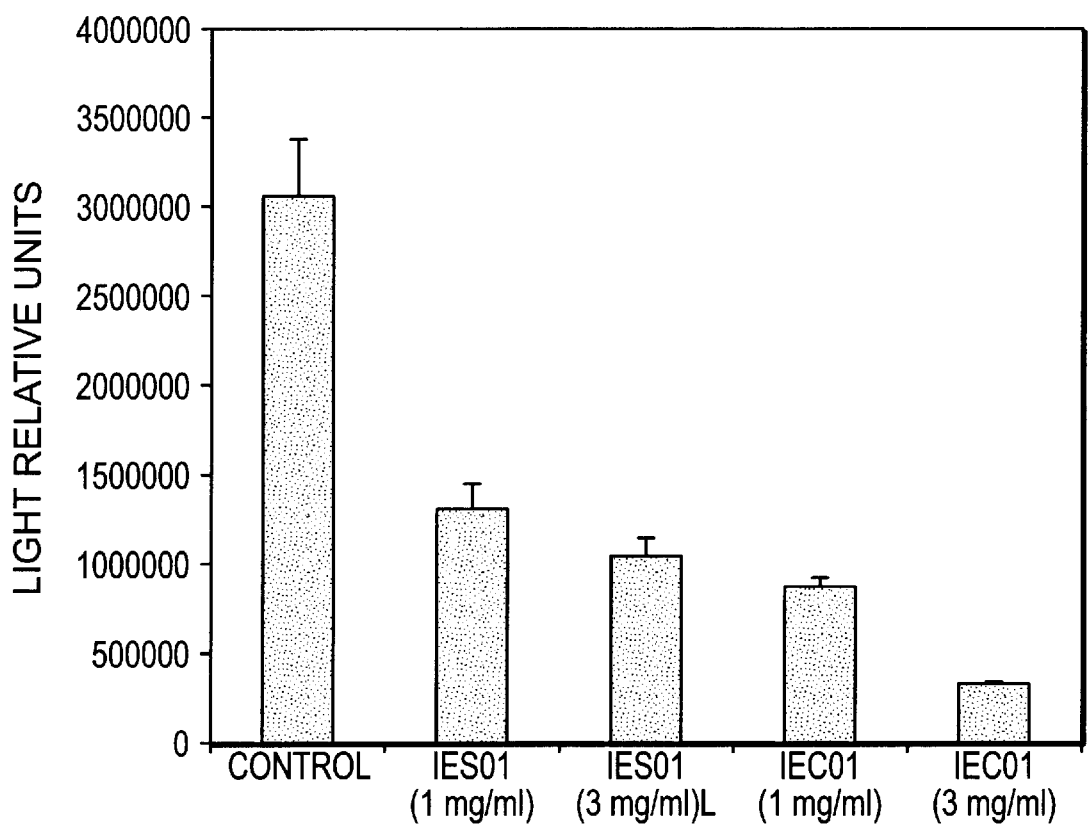

Values depicted in FIG. 2 represent the average of 4 parallel measurements for each individual group±SD and give the total amount of photons measured in 2 h.

Conclusions:

The results shown in FIG. 2 clearly indicate a drastic reduction in the amount of $O_2^-$ free radicals produced by macrophages treated with the compounds of the invention at the indicated doses as compared with untreated controls. The observed inhibition is doses dependent for both ELP used and is higher for IEC01 (FIG. 2).

3. In vivo Anti-inflammatory Activity: Inhibition of Bentonite-induced Skin Edema in Mice After demonstrating in vitro the inhibitory activity of the compounds of the invention on the expression of surface antigens like L-selectin, CD43 and CD44, which are directly involved in the initial step of leukocyte adhesion to the vascular endothelium and extravasation, and on the production of free superoxide radicals, we performed an additional study to determine the anti-inflammatory potential of the compounds of the invention in an in vivo animal system.

The aim of this study was to evaluate the anti-inflammatory activity of different doses of ELP in the system of bentonite-induced skin edema in mice, in comparison with Indomethacin, a potent commercial NSAID.

Method:

Mice were individually identified with an ear code and were kept in groups of 6 per cage (Makrolon: 47.6×22.7×14.5 cm). Each cage was individually labelled with the n°. of the study, type of treatment, doses used and route of administration, as well as the name of the director of the study, number and gender of contained animals, date of arrival and of the beginning of the experiment.

The animals had free access to mouse standard chow (UAR A04C; Usine d'Alimentation Rationelle, 91360-Villemoisson sur Orge, Francia; lot nos. 70520 and 70722). Drinking water access was ad libitum. The water, supplied by the Compañia de Aguas de Sabadell, S.A., is routinely analysed for the presence of possible contaminants. The temperature in the animal rooms was 22±3° C., with sporadic peaks of 26° C.; air humidity was 60±10%, with sporadic peaks of 80%. Daily light (between 7:00 h and 19:00 h) and dark phases were installed automatically.

Experimental Design:

Upon arrival, all animals were allowed to rest in the facilities for 8 days before use in the experiment. Table 2 indicates the six random groups of 10 mice each were set for experimentation.

TABLE 2

| Group | Treatment | Dosis (mg/kg) |
|-------|-----------|---------------|
| A | Inflammed control | — |
| B | Indomethacin | 2 |
| C | IES01 ($R_1 = C_{16}H_{33}$, $R_2 = CH_3$) | 2.5 |
| D | IES01 | 5 |
| E | IEC01 ($R_1 = C_{18}H_{37}$, $R_2 = CH_3$) | 2.5 |
| F | IEC01 | 5 |

The diameter of both hind pads of all mice was measured at day 0 and set as the basal value. Edema was then induced by injecting s.c. 13.3 mg/ml bentonite in 0.03 ml PBS into the right food pad. The corresponding mice were given daily the different compounds orally for 21 days. The analysed substances were given at the dosis indicated in the table each in 0.2 ml of PBS. The inflamed control group was given 0.2 ml PBS only. The diameter of hind pads, as well as the body weight, was then measured every other day.

Results:

In each experimental group the average value, the standard deviation (SD) and the standard error was determined for the two parameters studied (hind pad diameter and body weight). The factor variance analysis (FVA) was used to compare the values obtained in the different groups. Where statistically significant differences were observed, the Duncan-Kramer test for a $p<0.05$ was applied.

The data from the measurements of the food pads were plotted into the curves shown in FIGS. 3–6. The area below the curves corresponding to the diameters of the right and left pads was calculated and the evolution of the difference between them were plotted (FIGS. 7 and 8). The anti-inflammatory capacity of the different substances was evaluated as the extent of inhibition of the inflammatory process that was calculated with the formula $$\% \text{ of Inhibition} = \frac{C - T}{C} \times 100$$

where C is the area below the inflammed control group and T the area below the different treatment groups. The obtained results are depicted in Table 3.

TABLE 3

| Treatment | Dosis (mg/kg) | Area (A.U.) | Inhibition (%) |
|---|---|---|---|
| Inflamed control | — | 7.8 ± 0.97 | — |
| Indomethacin | 2 | 6.6 ± 0.92 | 15.3 |
| IES01 | 2.5 | 4.4 ± 0.63 | 43.8 |
| IES01 | 5 | 5.6 ± 0.70 | 28.3 |
| IEC01 | 2.5 | 5.9 ± 0.45 | 23.5 |
| IEC01 | 5 | 7.0 ± 1.34 | 9.7 |

Conclusions:

The experiments described demonstrate a higher anti-inflammatory capacity for the two ELP substances tested, as compared with the anti-inflammatory effect of indomethacin, except for the higher dosis of IEC01 (see table 3). At the lower dosis used for the ELPs (2.5 mg/kg), the stronger inhibitory potential is more evident, especially taking into account the lower molecular weight of indomethacin (Mr=433.8), as compared with IES01 (Mr= 573.8) and IEC01 (Mr=541.8). Thus, at the molecular level, IES01 and IEC01 are 3.8 times and 2 times more efficient, respectively, in inhibiting inflammation than indomethacin, one of the most potent NSAID commercially available.

Example 2

Absence of Inhibition of Prostagladins in Cell Lines

1. Inhibition of Prostaglandins ($PGE_2$) in Cell Lines.

As all NSAIDs tested so far have inhibitory effects on the activity of COX-1, COX-2 or both and thus interfere with the synthesis of cell protective Prostaglandins, and in particular the gut mucosa protective $PGE_2$, we checked for the possible inhibitory potential of the compounds of the invention in this system in comparison with some of the most potent commonly used NSAIDs. The analysis of the individual inhibitory potential on COX-1 and COX-2 revealed that the compounds of the invention, in contrast to the tested NSAIDs, have no effect on the production of $PGE_2$, and does not inhibit the expression of the constitutive and the inducible ciclooxygenase enzyme genes COX-1 and COX-2.

Methods:

Cell culture. Human promyelocytic HL-60 cells and promonocytic U937 cells were grown in RPMI-1640 culture medium supplemented with 10% (v/v) heat-inactivated fetal calf serum, 2 mM L-glutamine, 100 units/ml penicillin and 24 µg/ml gentamicin. Mouse 3T3 fibroblasts were grown in Dulbecco's modified Eagle's medium (DMEM) supplemented with 10% (v/v) heat-inactivated fetal calf serum, 2 mM L-glutamine, 100 units/ml penicillin and 24 µg/ml gentamicin. Cells were incubated at 37° C. in a humidified atmosphere at 5% $CO_2$ and 95% air.

Measurement of arachidonic acid release. Arachidonic acid release was measured as an assay for phospholipase $A_2$ ($PLA_2$) activity, because this enzyme activity constitutes the major pathway controlling arachidonic acid release. Cells ($5 \times 10^5$/ml) were labeled overnight with 0.1 µCi of [$^3$H] arachidonic acid/ml in RPMI-1640 culture medium containing 10% fetal calf serum. Then cells were washed four times with culture medium, and cells were resuspended in RPMI-160 culture medium in the absence of serum in the absence (control) or in the presence of distinct agents for the times indicated in the respective figures. After this period, cells were pelleted by centrifugation and supernatants were transferred to scintillation vials and counted for radioactivity. Results are shown as cpm of labelled arachidonic acid released to the extracellular medium.

Prostaglandin $E_2$ ($PGE_2$) measurement. 3T3 cells ($1.5 \times 10^5$ in 100 µl in complete DMEM culture medium) were incubated overnight at 37° C. (5% $CO_2$) in 96-well microtitre plates (tissue-culture grade). Then, the distinct agents were added in 100 µl complete DMEM culture medium for 20 min at 37° C. After washing thoroughly the cells with PBS, cells were lysed and intracellular $PGE_2$ was measured using an enzyme immunoassay kit (Amersham Pharmacia Biotech, Buckinghamshire, UK) following the manufacturer's instructions. Data obtained in duplicate measurements were converted into actual amounts of $PGE_2$ using a calibration curve run in parallel with defined amounts of $PGE_2$.

Reverse transcriptase polymerase chain reaction (RT-PCR). Total RNA was extracted from human neutrophils and cell lines using TRIZOL reagent (GIBCO-BRL) following the manufacturer's instructions. RNA preparations were carefully checked by gel electrophoresis and found to be free of DNA contamination. For the RT reaction, total RNA (10 µg) was primed with oligo-dt and reverse-transcribed into cDNA with 30 units of M-MLV reverse transcriptase from Promega according to manufacturer's instructions in a final volume of 20 µL. The mixture was incubated at 37° C. for 90 min. The generated cDNA was used for the semi-quantitative RT-PCR and the β-actin gene was used as an internal control. The generated cDNA was amplified by using primers for human $cPLA_2$ (5'-GTGTGAAAA-CATTTCCTGTA-3' and 5'-TAGCACAATCCAGAATTC CT-3'), COX-1 (5'-GAGCGTCAGTATCAACTGCG-3' and 5'-ATTGGAACTGGACAC CGAAC-3'), COX-2 (5'-TTCAAATGAGATTGTGGGAAAATTGCT-3' and 5'-AGATCATCTCTGCCTGAGTATCTT-3'), and β-actin (5'-CTGTCTGGCGGCACCA CCAT-3' and 5'-GCAACTAAGTCATAGTCCGC-3'). A 50-µL PCR mixture contained 2 µl of the RT reaction, 20 pmol of each primer, each dNTP (0.2 mmol/L), 10 mmol/L Tris-HCl (pH 8.3), 50 mmol/L KCl, 1.5 mmol/L $MgCl_2$, and 2.5 units of EcoTaq DNA polymerase derived from *Thermus aquaticus*. Primers were designed using the PCgene program for DNA analysis from Intelligenetics (Mountain View, Calif., USA) and the Primer3 program (Roze S and Skaletsky H J, Whitehead Institute for Biomedical Research, MIT Center for Genome Research, Mass.). The conditions for PCR amplification of cDNA were as follows: one cycle at 95° C. for 5 min as an initial denaturation step; then, denaturation at 95° C. for 30 s, annealing for 30 s, and extension at 72° C. for 60 s (the number of cycles was 28); followed by further incubation for 15 min at 72° C. (one cycle). The annealing step was carried out at 50° C. ($cPLA_2$), 63° C. (COX-1 and COX-2) or 69° C. (β-actin). After 20 cycles (β-actin) and 28 ($cPLA_2$ and COX-1), shown to be at the linear phase of amplification, the expected PCR products were size fractionated onto a 2% agarose gel in 1×TAE (40 mmol/L Tris-acetate, 1 mmol/L EDTA, pH 8.0), and stained with ethidium bromide. To analyze the expression of COX-2, an aliquot (2 µl) of the first PCR (28 cycles) was used for a second PCR round (28 cycles) in order to assess its expression.

Results and Conclusions:

In accordance with the invention it was found that the ELPs of the invention did not inhibit the $PGE_2$ production in murine fibroblasts 3T3. The results obtained upon 3T3 incubation with the compounds of the invention and the activating agent ionomycin, as well as with indomethacin are shown in Table 4.

TABLE 4

| Treatment | pg PGE$_2$ |
| --- | --- |
| Control | 112 ± 21 |
| Ionomycin (50 µM) | 486 ± 38 |
| IEC01 (10 µM) | 148 ± 22 |
| IES01 (10 µM) | 192 ± 25 |
| Indomethacin (50 µM) | 4 ± 2 |
| Ionomycin + Indomethacin | 3 ± 1 |
| IEC01 + Indomethacin | 5 ± 1 |
| IES01 + Indomethacin | 9 ± 3 |
| Ionomycin + IEC01 | 414 ± 30 |
| Ionomycin + IES01 | 461 ± 32 |

Upon treatment with ionomycin 3T3 fibroblasts produce large quantities of PGE$_2$, which are almost completely inhibited when indomethacin in added. This inhibition cannot be reversed by the addition of IEC01 or IES01. In contrast, no significant inhibition is observed after the addition of either IEC01 or IES01. The treatment of 3T3 cells with IEC01 or IES01 alone rather causes an increase of the basal levels of PGE$_2$ found in the control, whereas indomethacin completely abolishes this production. Together, the data shown in the table above clearly demonstrate that the ELPs IEC01 and IES01 do not interfere with the acute production of PGE$_2$ and, if at all, contribute to increased levels of the constitutive, basal production of PGE$_2$. In addition, using a semiquantitative RT-PCR detection assay, we demonstrate that the levels of expression of the genes encoding for COX-1 and COX-2 were not affected by the treatment with ELPs of two different cell lines, HL60 (FIG. 9) and the astrocytoma cell line 1231N1 (data not shown). Furthermore, IEC01 did not affect the mRNA expression of cytosolic PLA$_2$, as measured by semiquantitative RT-PCR (FIG. 9), and was able to stimulate PLA$_2$ activity, as measured by [$^3$H]arachidonic acid release (FIG. 10). The lack of inhibition of PLA$_2$ gene expression and activity is of importance as this enzymatic activity is the main regulator of the arachidonic level in the cell, which constitutes the precursor for prostaglandin synthesis.

2. Inhibition of Prostaglandins (PGE$_2$) in Human Gastric Mucosa.

Normal mucosal gastric biopsies were incubated which IEC01 and other agents ex vivo and mucosal prostaglandin E$_2$ (PGE$_2$) synthesis measured. Whereas indomethacin completely blocked PGE$_2$ generation, IEC01 did not inhibit PGE$_2$ synthesis. These data indicate that ET-18-OCH$_3$ spares gastric cyclo-oxygenase activity, unlike all the available nonesteroideal anti-inflammatory drugs (NSAIDs). These data indicate that IEC01 may have gastrointestinal toxicity than the known NSAIDs.

Methods:

The ability of the gastric mucosa to generate prostaglandins estimates total cyclooxygenase (COX) activity (COX-1 plus any COX-2). To measure ex vivo prostaglandin E$_2$ (PGE$_2$) synthesis, normal gastric mucosal biopsies were immediately placed in Ependorff tubes containing phosphate-buffered saline (PBS). Then fresh biopsies were pelled by centrifugation and washed with Hepes-glucose buffer (150 mM NaCl, 5 mM KCl, 10 mM Hepes, 1.2 mM MgCl$_2$, 1.3 mM CaCl$_2$, 5.5 mM glucose, pH 7.5). Each mucosal gastric biopsy was cut into different pieces (about 1 mg weight) that were subsequently weighed and incubated in the absence or in the presence of the distinct agents indicated in the corresponding Table for 20 min at 37° C. in 200 µl Hepes-glucose buffer. Then cells were mucosal gastric samples were pelleted by centrifugation, lysed and intracellular PGE$_2$ was measured using an enzyme immunoassay kit (Amersham Pharmacia Biotech, Buckinghamshire, UK) following the manufacturer's instructions. Prostaglandin synthesis is expressed as picograms of PGE$_2$ synthesised per mg of tissue incubation. Each experiment corresponded to the use of one biopsy, in order to avoid variability among different biopsies. Normal volunteers without a previous pharmacological treatment were selected for these assays. The normal gastroduodenal mucosa was visually assessed by endoscopy.

Results:

IEC01 did not inhibit the PGE$_2$ generation in human mucosal gastric biopsies. The effect of IEC01 on PGE$_2$ synthesis in human mucosal gastric biopsies, as well as the actions of the activating agent ionomycin and the prostaglandin synthesis inhibitor indomethacin, is shown in Table 5.

As shown in Table 5, ionomycin induced an increase in the mucosal gastric PGE$_2$ production, whereas indomethacin blocked completely the generation of PGE$_2$. The compound IEC01 induced a weak increase in PGE$_2$ production. Addition of indomethacin blocked the PGE$_2$ production induced by ionomycin, but IEC01 did not inhibit the ionomycin induced PGE$_2$ generation. No currently marketed NSAID, even those that are COX-2 selective, spare gastric COX activity at therapeutic concentrations. Therefore, it can be envisaged that IEC01 have less gastrointestinal toxicity than the known NSAIDs, since they all block gastric PGE$_2$ production.

TABLE 5

| Treatment | pg PGE$_2$/mg (weight) |
| --- | --- |
| Control | 115 ± 26 |
| IEC01 | 131 ± 29 |
| Ionomycin | 308 ± 31 |
| Indomethacin | 7 ± 2 |
| IEC01 + Ionomycin | 322 ± 47 |
| IEC01 + Indomethacin | 17 ± 6 |
| Ionomycin + Indomethacin | 8 ± 3 |

Human mucosal gastric biopsies were cut into about 1 mg pieces, incubated with the indicted agents (10 µM) for 20 min at 37° C. in Hepes-glucose buffer, and then the intracellular content of PGE$_2$ was determined as described in the Methods section. Untreated control samples were run in parallel. Data are shown as mean Values+S.D. from three independent experiments.

Example 3

In vivo Inhibition of Ulcerative Colitis

The compounds used in accordance with the invention show a therapeutic potential in the treatment of bowel inflammatory diseases including ulcerative colitis and Crohn's disease. The NSAIDs fail to efficiently treat Crohn's disease, ulcerative colitis and other bowel inflammatory diseases.

The therapeutic potential for the treatment of ulcerative colitis of IEC01 at 2.5 and 5 mg/kg and IES01 at 2.5 mg/kg, was evaluated after their administration by oral route during 14 days (7 days of preventive treatment and 7 days of therapeutic treatment) using the rat model of experimental colitis induced by TNB (2,4,6-trinitrobenzenesulphonic acid). As reference parameters, the body weight, wet colon weight and score macroscopic evaluation were evaluated after 24 hours and after 7 days of the intraluminal administration of TNB in the colon.

An ethanol control group showed an acute bowel inflammation at 24 hours. After 7 days of the intraluminal administration of 30% ethanol in the colon, the inflammatory effect decreased and the reference parameters values are similar to those of the blank control group (Tables 7 and 8).

The colitis control group showed an inflammatory response 24 hours after the intraluminal administration of 20-mg TNB (0.57 ml 30% ethanol) in the colon. The inflammatory response is recognised by the presence of ulcerative fissures, faecal shatters and inflammation of bowel wall. A chronic inflammatory response was observed 7 days after the administration. An erratic response with lineal or punctual ulcers, necrosis, faecal shatters, reduction of colonic lumen, granulomas and peritoneal adherence was observed.

The IEC01 was administered by oral route at daily doses of 2.5 and 5 mg/kg doses. Both dosages showed remarkable anti-inflammatory activity with decrease of the wet weight of colon (p<0.05, Ducan-Kramer Test at 24 hours) and the severity of mucosal damage versus the ulcerative colitis control group. In the macroscopic evaluation at 24 hours post-administration, the highest inhibitory activity was observed when IEC01 was used at a 5-mg/kg dose. Nevertheless, after 7 days treatment the inhibitory activity of IEC01 (score) was 78,6% and 71,4% when this compound was used at 2.5 and 5 mg/kg, respectively.

The IES01 administered by oral route at 2.5 mg/kg dose showed marked anti-inflammatory activity at 24 hours after the.intraluminal administration in the colon, reducing the colon wet weight and the damaged score associated to this disease. The score of IES01 at 2.5 mg/kg after 7 days of treatment shows a 50% inhibition.

TABLE 6

Body weight evaluation in Wistar rat (g).
Mean values (Mean ± SEM)

| TREATMENT | DAY 1 | DAY 2 | DAY 4 | DAY 7 | DAY 8 | DAY 11 | DAY 12 | DAY 13 | DAY 14 |
|---|---|---|---|---|---|---|---|---|---|
| CONTROL BLANK | 233.6 ± 3.74 | 234.0 ± 3.63 | 238.7 ± 3.36 | 209.8 ± 2.87 | 235.3 ± 2.95 | 242.8 ± 4.16 | 250.2 ± 6.80 | 256.2 ± 5.93 | 259.8 ± 5.28 |
| CONTROL ETHANOL | 232.1 ± 3.03 | 233.0 ± 3.48 | 240.7 ± 3.74 | 209.0 ± 2.88 | 227.62 ± 2.70 | 237.2 ± 7.17 | 245.0 ± 7.78 | 248.4 ± 7.45 | 250.0 ± 7.83 |
| CONTROL COLITIS | 230.7 ± 2.05 | 233.6 ± 2.51 | 239.2 ± 3.04 | 210.2 ± 2.16 | 218.3 ± 2.89 | 231.2 ± 7.11 | 240.6 ± 8.23 | 241.4 ± 8.95 | 242.2 ± 8.13 |
| IEC01 2.5 mg/Kg p.o. | 233.5 ± 3.07 | 236.0 ± 3.42 | 240.3 ± 3.60 | 210.6 ± 3.05 | 214.8 ± 3.41 | 234.4 ± 4.53 | 241.0 ± 4.04 | 244.2 ± 4.16 | 249.4 ± 4.42 |
| IEC01 5.0 mg/Kg p.o | 227.4 ± 1.21 | 229.1 ± 1.05 | 235.9 ± 1.63 | 207.4 ± 1.90 | 216.2 ± 2.56 | 237.6 ± 3.35 | 245.2 ± 3.17 | 250.6 ± 3.31 | 253.6 ± 5.34 |
| IES01 2.5 mg/Kg p.o. | 232.3 ± 2.68 | 234.5 ± 2.94 | 241.9 ± 2.40 | 211.4 ± 2.48 | 218.8 ± 3.57 | 244.4 ± 4.95 | 250.0 ± 4.72 | 249.8 ± 6.84 | 254.0 ± 8.44 |

TABLE 7

Macroscopic evaluation in Wistar rat (Mean ± SEM)

Macroscopic evaluation after 24 hours of intraluminal Administration in the colon

| Treatment | Wet Weight | % | Weight/mm | % | Sample 2 × 6 mm (mg) | % | Score (0–10) | % |
|---|---|---|---|---|---|---|---|---|
| CONTROL BLANK | 0.800 ± 0.04 | | 0.086 ± 0.00 | | 95.26 ± 5.18 | | 0.0 ± 0.00 | |
| CONTROL ETHANOL | 1.269 ± 0.19 | | 0.140 ± 0.02 | | 242.38 ± 40.97 | | 2.0 ± 0.71 | |
| CONTROL COLITIS | 1.700 ± 0.05 | | 0.213 ± 0.02 | | 395.72 ± 58.42 | | 5.5 ± 0.59 | |
| IEC01 2.5 mg/Kg p.o. | 1.689 ± 0.15 | 35.1 | 0.187 ± 0.02 | 35.2 | 373.12 ± 48.12 | 14.7 | 5.2 ± 0.73 | 8.6 |
| IEC01 5.0 mg/Kg p.o. | 1.412 ± 0.06 | 77.4 | 0.157 ± 0.00 | 77.3 | 301.10 ± 18.95 | 61.7 | 4.0 ± 0.32 | 42.9 |
| IES01 2.5 mg/kg p.o. | 1.425 ± 0.20 | 75.3 | 0.158 ± 0.02 | 75.2 | 272.70 ± 44.43 | 80.2 | 3.2 ± 0.86 | 65.7 |

TABLE 8

Macroscopic evaluation in Wistar rat (Mean ± SEM)

Macroscopic evaluation after 7 days of intraluminal Administration in the colon

| Treatment | Wet Weight | % | Weight/mm | % | Sample 2 × 6 mm (mg) | % | Score (0–10) | % |
|---|---|---|---|---|---|---|---|---|
| CONTROL BLANK | 0.718 ± 0.03 | | 0.085 ± 0.003 | | 110.46 ± 9.54 | | 0.0 ± 0.00 | |

TABLE 8-continued

Macroscopic evaluation in Wistar rat (Mean ± SEM)

Macroscopic evaluation after 7 days of intraluminal Administration in the colon

| Treatment | Wet Weight | % | Weight/mm | % | Sample 2 × 6 mm (mg) | % | Score (0–10) | % |
|---|---|---|---|---|---|---|---|---|
| CONTROL ETHANOL | 0.933 ± 0.93 | | 0.104 ± 0.10 | | 138.56 ± 9.77 | | 0.6 ± 0.60 | |
| CONTROL COLITIS | 1.419 ± 0.20 | | 0.157 ± 0.02 | | 301.26 ± 62.30 | | 3.4 ± 0.87 | |
| IEC01 2.5 mg/Kg p.o. | 1.354 ± 0.14 | 13.4 | 0.150 ± 0.00 | 13.3 | 299.62 ± 75.58 | 17.9 | 1.2 ± 0.58 | 78.6 |
| IEC01 5.0 mg/Kg p.o. | 1.113 ± 0.14 | 63.0 | 0.124 ± 0.01 | 63.0 | 272.14 ± 53.65 | 71.4 | 1.4 ± 0.40 | 71.4 |
| IES01 2.5 mg/kg p.o. | 1.365 ± 0.24 | 11.1 | 0.151 ± 0.03 | 11.1 | 185.04 ± 23.18 | 31.7 | 2.0 ± 0.84 | 50.0 |

What is claimed is:

1. A method for the prevention or treatment of an inflammatory disease comprising administering an effective amount of formula (I):

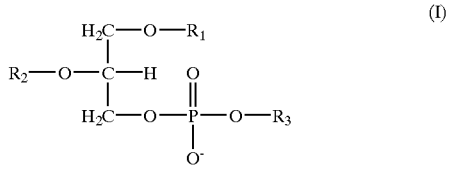

wherein $R_1$ is a $C_{12}$–$C_{18}$ straight or branched alkyl group; $R_2$ is $C_1$–$C_8$ straight or branched alkyl group; and $R_3$ is:

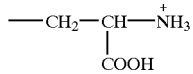

or the salts, enantiomers and diastereomers thereof, to a patient in need thereof.

2. The method according to claim 1, wherein $R_1$ is a $C_{16}$–$C_{18}$ straight alkyl group and $R_2$ is methyl.

3. The method according to claim 2, wherein the compound of formula (I) is:

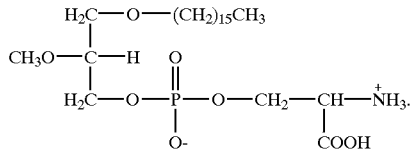

4. The method according to claim 1, wherein said inflammatory disease is a chronic inflammatory disease.

5. The method according to claim 4, wherein said chronic inflammatory disease is associated with an inflammatory bowel disease.

6. The method according to claim 5, wherein said inflammatory bowel disease is selected from the group consisting of ulcerative colitis, Crohn's disease, a gastric ulcer and a duodenal ulcer.

7. The method according to claim 4, wherein said chronic inflammatory disease is associated with an inflammatory disease of the respiratory airways.

8. The method according to claim 7, wherein said inflammatory disease of the respiratory airways is asbestosis or silicosis.

9. The method according to claim 4, wherein said chronic inflammatory disease is associated with inflammatory processes derived from alcoholic liver.

10. The method according to claim 9, wherein said alcoholic liver is cirrhosis of the liver.

11. The method according to claim 4, wherein said chronic inflammatory disease is associated with another inflammatory disease selected from the group consisting of pemphigus vulgaris, polymyositis-dermatomyositis, Sjögrensyndrome, Lyme disease, lupus erythematosus and Behcet's disease.

12. The method according to claim 1, wherein said inflammatory disease is associated with an ulcerative condition of the gastrointestinal tract.

13. The method according to claim 12, wherein said ulcerative condition is associated with an inflammatory bowel disease.

14. The method according to claim 1, wherein said inflammatory disease is an acute inflammatory disease.

15. The method according to claim 14, wherein said acute inflammatory disease is associated with infective diseases, non-rheumatic inflammation or other inflammatory lesions of traumatic and/or sportive origin.

16. The method according to claim 15, wherein said non-rheumatic inflammation is selected from the group consisting of bursitis, synovitis, cap sulitis and tendinitis.

17. A method for the prevention or treatment of chronic inflammatory diseases associated with (a) ulcerative conditions of the gastrointestinal tract, (b) inflammatory bowel diseases, (c) inflammatory diseases of the respiratory airways, (d) inflammatory processes derived from alcoholic liver, or (e) another inflammatory disease selected from the group consisting of pemphigus vulgaris, polymyositis-dermatomyositis, Sjögren-syndrome, Lyme disease, lupus erythematosus and Behcet's disease comprising administering an effective amount of formula (I):

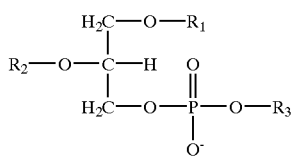

(I)

wherein $R_1$ is a $C_{12}$–$C_{18}$ straight or branched alkyl group;
$R_2$ is $C_1$–$C_8$ straight or branched alkyl group; and $R_3$ is:

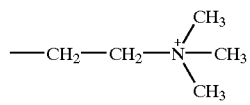

or the salts, enantiomers and diastereomers thereof, to a patient in need thereof.

18. The method according to claim 17, wherein $R_1$ is a $C_{16}$–$C_{18}$ straight alkyl group and $R_2$ is methyl.

19. The method according to claim 17, wherein the compound of formula (I) is:

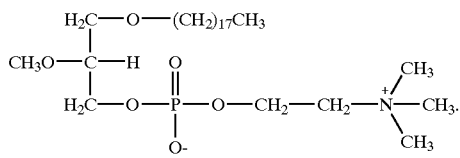

20. The method according to claim 17, wherein said inflammatory bowel disease is selected from the group consisting of ulcerative colitis, Crohn's disease, a gastric ulcer and a duodenal ulcer.

21. The method according to claim 17, wherein said inflammatory disease of the respiratory airways is asbestosis or silicosis.

22. The method according to claim 17, wherein said alcoholic liver is cirrhosis of the liver.

23. The method according to claim 17, wherein said ulcerative condition is associated with an inflammatory bowel disease.

* * * * *